United States Patent [19]

Thomas et al.

[11] Patent Number: 5,098,918

[45] Date of Patent: Mar. 24, 1992

[54] 1,2,3-THIADIAZOLE COMPOUNDS, COMPOSITIONS AND METHOD OF ANTI-THROMBOTIC TREATMENT

[75] Inventors: Edward W. Thomas, Kalamazoo; Ronald H. Rynbrandt, deceased, late of Portage, both of Mich., by LeAnna C. Heckman, personal representative;

[73] Assignee: The Upjohn Company, Kalamazoo, Mich.

[21] Appl. No.: 58,630

[22] Filed: Jun. 4, 1987

Related U.S. Application Data

[63] Continuation of Ser. No. 735,497, May 17, 1985, abandoned, which is a continuation-in-part of Ser. No. 434,146, Oct. 13, 1982, abandoned, and Ser. No. 618,987, Jun. 11, 1984, abandoned.

[51] Int. Cl.$^5$ ............... C07D 285/06; A61K 31/11
[52] U.S. Cl. ............................ 514/361; 548/127
[58] Field of Search ...................... 548/127; 514/361

[56] References Cited

U.S. PATENT DOCUMENTS

| | | | |
|---|---|---|---|
| 3,629,071 | 12/1971 | Sekhar | 195/1.8 |
| 3,654,294 | 4/1972 | Lemieux et al. | 260/302 A |
| 3,940,407 | 2/1976 | Muchowski et al. | 260/302 |
| 4,168,315 | 9/1979 | Rynbrandt et al. | 424/270 |
| 4,177,054 | 12/1979 | Arndt et al. | 71/90 |
| 4,253,864 | 3/1981 | Kloek | 7/190 |

FOREIGN PATENT DOCUMENTS 2728523 12/1979 Fed. Rep. of Germany.

OTHER PUBLICATIONS

Chemical Abstracts, 88: 50737h.
Trickes, Georg et al., Justus Liebigs Ann. Chem., 1977 (8), 1347-53.
Chemical Abstracts, 84: 150569r.
Ulm, Von Klaus et al., Angew. Chem., 87, pp. 171-172 (1975).
Raap R., et al., Can. J. Chem., 46, pp. 1057-1063 (1968).
Hurd, Charles D., et al., "On Acylhydrazones and 1,2,4-Thiadiazoles", J. Am. Chem. Soc., 77, pp. 5359-5364 (1955).
Shafiee A., et al., J. Het. Chem. 10, pp. 11-14 (1973).
Ramsby, S. I., et al., "Sedative 1,2,3-Thiadiazoles", Acta. Pharm. Suec., 10, pp. 285-296 (1973).
Millard, B. J., et al., "High Resolution Mass Spectrometry, Part VII, 1,2,3-Thiadiazole Derivatives", J. Chem. Soc., C., pp. 2042-2045 (1970).
Shafiee, A., et al., "Kinetic Studies of Nucleophilic Substitution of Various Halothiadiazoles with Methoxide Ion", J. Het. Chem., 11, pp. 343-345 (1974).
Lewis, Graham S., et al., "3-[(1,2,3-Thiadiazol-5-ylthio)methyl]cephalosporins", J. Med. Chem., 22, pp. 1214-1218 (1979).
Chemical Abstracts, 90, 137833b.
Gil, D. L., et al., Pestic. Biochem. Physiol., vol. 7, pp. 183-193 (1977).
Shio, Hideo et al., "Prostaglandin $E_1$ in Platelet Harvesting: An in vitro Study", Science, vol. 175, pp. 536-542 (Feb. 4, 1972).
Bygdeman, S. et al., "Studies of Platelet Adhesiveness, Blood Viscosity & the Microcirculation in Patients with Thrombotic Disease", J. Atheroscler. Res., vol. 10, pp. 33-38 (1969).

Primary Examiner—Robert Gerstl
Attorney, Agent, or Firm—William G. Jameson; John J. Killinger

[57] ABSTRACT

Novel 1,2,3-thiadiazole compounds, new and old 1,2,3-thiadiazole compositions and method of anti-thrombotic treatment are systemically administered to a human or animal.

14 Claims, No Drawings

1

1,2,3-THIADIAZOLE COMPOUNDS, COMPOSITIONS AND METHOD OF ANTI-THROMBOTIC TREATMENT

CROSS-REFERENCE TO RELATED APPLICATION

This is a continuation of Ser. No. 735,497 filed 5-17-85, abandoned which is continuation -in-part of co-pending application Ser. No. 434,146, filed Oct. 13, 1982 and application Ser. No. 681,987, filed June 11, 1984, now abandoned.

BACKGROUND OF THE INVENTION

U.S. Pat. No. 4,168,315 was considered in preparing this patent application. U.S. Pat. No. 4,168,315 discloses dianisyl thiazole compounds as useful for anti-thrombotic treatment.

ADDITIONAL BACKGROUND

U.S. Pat. No. 3,940,407 discloses 4-(monohydroxyphenyl)-5-phenyl-1,2,3-thiadiazoles, specifically 4-(2-hydroxyphenyl)-5-phenyl-1,2,3-thiadiazole and 4-(4-hydroxyphenyl)-5-phenyl-1,2,3-thiadiazole. See formula X in column 6, line b 40 and column 16, lines 32-34.

Chemical Abstracts 88: 50737h disclosed 4-(4-methoxyphenyl)-5-(2-methoxyphenyl)-1,2,3-thiadiazole. See also Justus Liebigs Ann. Chem., 1977, (8), 1347-53 and chemical Abstracts 84: 150569r.

U.S. Pat. No. 4,253,864 discloses substituted-1,2,3-thiadiazoles, including generically 4-(lower alkyl, trifluoromethyl, naphthyl pyridiyl, thienyl, phenyl and substituted phenyl containing from one to three substituents individually selected from the class consisting of lower alkyl, lower alkoxy, halogen, nitro and trifluoromethyl)-5-phenyl-1,2,3-thiadiozoles, as safening agents useful to reduce herbicidal injury to treated crop plants.

There are many other examples of 1,2,3-thiadiazoles in the literature, including 4,5-bis-(4-chlorophenyl)-1,2,3-thiadiazole disclosed in Angew. Chem., 87, 171-172 (1975) and 4-phenyl-1,2,3-thiadiazole, 5-phenyl-1,2,3-thiadiazole, 4-(4-chlorophenyl)-1,2,3-thiadiazole, 4(4-methoxyphenyl)-1,2,3-thiadiazole and 4,5-bis-phenyl-1,2,3-thiadiazole disclosed in Can. J. chem., 46, 1057-1063 (1968) and J. Am. Chem. Soc., 77, 5359-5364 (1955); 4-(4-methylphenyl)-1,2,3-thiadiazole is disclosed in J. Het. Chem. 10, 11-14 (1973). U.S. Pat. No. 3,654,294 disclosed 4-(5-isothiazole)-1,2,3-thiadiazole, Acta. Pharm. Suec., 10, 285-296 (1973) discloses 4-methyl-1,2,3-thiadiazole and 4-butyl-1,2,3-thiadiazole. J. Chem. Soc. C., 2042-5 (1970) discloses 5-amino-1,2,3-thiadiazole. J. Het Chem., 11, 343-345 (1974) discloses 4-phenyl-5-chloro-1,2,3-thiadiazole.

A few examples illustrating the diverse biological activity of 1,2,3-thiadiazoles include:

J. Med. Chem., 22, 1214-1218 (1979) which discloses 3-(1,2,3-Thiadiazol-5-ylthio)methyl)aphalosporins at antibacterial agent; Chem. Abstr., 90 137833B (1979) German Patent 2728523, which discloses 1,2,3-Thiadiazole-5-carboxylic acid derivatives as herbicidal and growth-regulatory compounds; Pestic. Biochem. Physiol., 7, 183-193 (1977) which discloses 1,2,3-Benzothiadiazoles as insecticide synergists for inhibition of microsomal oxidation.

Ronald H. Rynbrandt, now deceased, first synthesized 4,5-bis(p-methoxyphenyl)-1,2,3-thiadiazole and submitted it for evaluation of anti-thrombotic activity.

BRIEF DESCRIPTION OF THE INVENTION

This invention relates to novel compounds of the Formula I and to a broad group of compounds, Formulae I or II which are useful in association with a pharmaceutical carrier for the in vitro and in vivo inhibition of platelet adhesiveness and platelet aggregation and prevention or treatment of diseases arising from platelet adhesiveness and platelet aggregation, more particularly thrombotic disease states such as myocardial infarct, cerebrovascular strokes and pulmonary thrombus formation.

DETAILED DESCRIPTION OF THE INVENTION

For in vivo applications, the compositions of the present invention are presented for administration to humans and animals in unit dosage forms, such as tablets, capsules, pills, powders, granules, sterile parental solutions or suspensions, and oral solutions or suspensions, and oil-in-water and water-in-oil emulsions containing suitable quantities of the compound of Formulae I or II.

For oral administration either solid or fluid unit dosage forms can be prepared. For preparing solid compositions such as tablets, the compound of Formulae I or II is mixed with conventional ingredients such as talc, magnesium stearate, dicalcium phosphate, magnesium aluminum silicate, calcium sulfate, starch, lactose, acacia, methylcellulose and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using an aqueous-alcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

For in vitro applications, aqueous solutions are prepared by dissolving a compound of the Formulae I or II in water and adding salt to provide an isotonic solution and buffering to a pH compatible with blood.

Advantageously, the composition prepared for parenteral administration can be used when prepared omitting the local anesthetic.

The dosage for humans and animals depends on the blood volume and condition of the subject. A dosage schedule of from about 1.0 to about 500 mg. per dose administered 1 to 3 times daily is effective for reducing platelet aggregation in the subject. Expressed in terms of weight, the dose can be from 0.01 to 30 mg/kg/day.

For in vitro, dosage is from 0.001 to 5 micrograms/ml of whole blood.

The addition of compounds of the Formulae I or II to whole blood provide in vitro applications of the invention such as in the storage of whole blood in blood banks, and whole blood to be used in heart-lung machines. Additionally, whole blood containing a compound of the Formulae I or II can be circulated through organs, e.g., heart and kidneys, which have been removed from a cadaver and prior to transplant.

The compounds of the Formulae I or II can also be used for the preparation of stable platelet-rich plasma concentrates in the same manner as the prostaglandins as disclosed in U.S. Pat. No. 3,629,071 and Science, vol. 175, pp. 536-542 (Feb. 4, 1972).

In vivo applications are: the administration to humans and animals to prevent clot formation in situations such as following surgery to prevent postoperative thrombosis; in geriatric patients to prevent transient cerebral ischemic attacks; and long-term prophylaxis following myocardial infarcts and strokes.

In general a compound of the Formulae I or II is usefully administered prophylactically to humans having a platelet adhesiveness value in excess of 25 percent [Bygdeman et al., J. Atheroscler. Res., 10, 33-39 (1969)].

EXAMPLE 1

A lot of 10,000 tablets, each containing 50 mg of 4,5-bis-4-methoxyphenyl)-1,2,3-thiadiazole is prepared from the following types and amounts of ingredients:

| | |
|---|---|
| 4,5-Bis-(4-methoxyphenyl)-1,2,3-thiadiazole | 500 gm |
| Dicalcium phosphate | 1,500 gm |
| Methylcellulose, U.S.P. (15 cps.) | 60 gm |
| Talc | 150 gm |
| Corn starch | 200 gm |
| Calcium stearate | 12 gm |

The dicalcium phosphate and the active ingredient are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing thrombus formation at a dose of 1 tablet every 4 hours following surgery.

EXAMPLE 2

One thousand two-piece hard gelatin capsules, each containing 100 mg of:

| | |
|---|---|
| 4,5-Bis-(4-methoxyphenyl)-1,2,3-thiadiazole | 100 gm |
| Talc | 100 gm |
| Magnesium stearate | 10 gm |

The ingredients are mixed well and filled into capsules of the proper size.

Capsules so prepared are useful in preventing further coronary infarcts at a dose of 1 capsule daily to a patient recovering from a coronary infarct.

EXAMPLE 3

One thousand tablets, each containing 400 mg of 4,5-bis-(4-methoxyphenyl)-1,2,3-thiadiazole are made from the following types and amounts of ingredients:

| | |
|---|---|
| 4,5-Bis-(4-methoxyphenyl)-1,2,3-thiadiazole | 400 gm |
| Microcrystalline cellulose NF | 120 gm |
| Corn starch | 16 gm |
| Magnesium stearate powder | 4 gm |

The ingredients are screened and blended together and pressed into 240 mg tablets.

The tablets are useful to protect against transient cerebral ischemic attacks at a dose of 1 tablet daily.

EXAMPLE 4

A sterile preparation suitable for intramuscular injection and containing 50 mg of 4,5-bis-(4-methoxyphenyl)-1,2,3-thiadiazole in each milliliter is prepared from the following ingredients:

| | |
|---|---|
| 4,5-Bis-(4-methoxyphenyl)-1,2,3-thiadiazole | 50 gm |
| Benzyl benzoate | 200 ml |
| Methylparaben | 1.5 gm |
| Propylparaben | 0.5 gm |
| Cottonseed oil q.s. | 1,000 ml |

One milliliter of this sterile preparation is injected for prophylactic treatment prior to surgery.

EXAMPLE 5

Sic hundred ml of an aqueous solution containing 0.1 mg of 4,5-bis-(4-methoxyphenyl)-1,2,3-thiadiazole acid per ml is prepared as follows:

| | |
|---|---|
| 4,5-Bis-(4-methoxyphenyl)-1,2,3-thiadiazole | 60 mg |
| Sodium chloride | 5,400 mg |
| Water for injection q.s. | 600 ml |

The 4,5-bis-(4-methoxyphenyl)-1,2,3-thiadiazole and sodium chloride are dissolved in sufficient water to make 600 ml of sterile filtered.

The solution is added to whole blood 16.0 ml/liter for use in a heart-lung machine.

EXAMPLE 6

Following the procedure of the preceding Examples 1 through 5, inclusive, compositions are similarly prepared substituting an equal amount of 5-(4-methoxyphenyl)-4-(4-(methylthio)-phenyl)-1,2,3-thiadiazole, 5-(4-methoxyphenyl)-4-phenyl-1,2,3-thiadiazole, 4-(4-methoxyphenyl)-5-phenyl-1,2,3-thiadiazole, 4,4'-(1,2,3-thiadiazole-4,5-diyl)bis(N,N-dimethyl)-benzeneamine, for the 4,5-bis-(4-methoxyphenyl)-1,2,3-thiadiazole of Example 6.

EXAMPLE 7

5-Phenyl-1,2,3-thiadiazole (1)

A mixture of tosylhydrazine (18.3 g, 0.1 mol) and phenylacetaldehyde (12.0 g, 0.1 mol) was heated in 60% aqueous MeOH (30 ml) to 60° C., then cooled and stored at 0° C. for 18 hours. The solid was filtered, washed with 60% aqueous MeOH and recrystallized from MeOH affording the hydrazone (16.39 g, 57%), m.p. 118°-119° C.

A solution of thionyl chloride (5 ml, 70 mmol) and $CH_2Cl_2$ (30 ml) was cooled to 0° C. and tosylhydrazone (10.0 g, 35 mmol) dissolved in 100 ml of $CH_2Cl_2$ was added. The reaction was warmed to room temperature and kept at this temperature for 17 hours. The reaction was quenched by pouring over 50 g of ice and the solvent was removed under vacuum. THF (100 ml) was added to the mixture and heated at reflux for 24 hours. The aqueous portion was extracted with $2 \times 25$ ml of $Et_x$). Combined organic fractions and extracted with $2 \times 25$ ml of 10% aqueous NaOH, dried and concentrated yielding 6.2 g of crude material.

This material was bulb to bulb distilled at 90°-100° C. (0.2 mm) to afford 1 (2.0 g, 35%), m.p. 46°-48° C. The pot residue was chromatographed to yield an additional 0.5 g of 1, m.p. 46°-48° C.

Analysis: Calc'd for $C_8H_6N_2S$: C, 59.23; H, 3.73; N, 17.27; S, 19.76. Found: C, 58.94; H, 3.84; N, 17.19; S, 20.20.

EXAMPLE 8

4-Phenyl-1,2,3-thiadiazole (2)

A solution of acetophenone (12.0 g, 0.1 mol), tosylhydrazine (18.6 g, 0.1 mol), a spatula tip of TsOH and toluene were heated at reflux with azeotropic removal of water until all the ketone had been consumed as determined by TLC. The solvent was removed under vacuum and the residue was recrystallized from MeOH to afford the tosylhydrazone (23.7 g, 82%), m.p. 146°-146.5° C.

Thionyl chloride (50 ml) was cooled to 0° C. and the tosylhydrazone (21.0 g, 73 mmol) was added. The reaction was warmed to 60° C. for 1 hour and then cooled and the excess thionyl chloride was removed under vacuum. Eighty percent aqueous THF was added and the mixture was heated at reflux for 16.5 hours. Saturated aqueous NaCl was added, and the mixture was extracted with $2 \times 25$ ml portions of $Et_2O$. After drying and concentration, the organic fraction afforded a brown solid which when recrystallized from $Et_2O$, yielded 2 (9.1 g, 77%), m.p. 75°-77° C.

Analysis: Calc'd for $C_8H_6N_2S$: C, 59.23; H, 3.73; N, 17.27; S, 19.77. Found: C, 58.98; H, 3.86; N, 17.58; S, 19.96.

EXAMPLE 9

4,5-Diphenyl-1,2,3-thiadiazole (3)

A mixture of α-phenylacetophenone (39.25 g, 0.2 mol), tosylhydrazine (37.2 g, 0.2 mol) and 60% aqueous MeOH was heated at reflux for 1 hour and cooled. The solid was filtered and washed with 60% aqueous MeOH. The solid was dried in a vacuum oven overnight affording the tosylhydrazone (62.2 g, 85%), m.p. 150°-152° C.

The tosylhydrazone (58.0 g, 0.16 mol) was dissolved in $CH_2Cl_2$ (200 ml) and thionyl chloride (14.1 ml, 0.2 mol) in $CH_2Cl_2$ (10 ml) was added and the entire reaction was stirred at room temperature 2.25 hours. Filtration of the mixture afforded 9.0 g of solid identified by NMR as toluenesulfonylchloride. The remaining liquid was concentrated and then heated at reflux in THF (200 ml) and $H_2O$ (50 ml) for 20.5 hours. After cooling, it was brought to pH 11 with NaOH. The aqueous layer was extracted with $2 \times 50$ ml portions of $Et_2O$. Drying and evaporation yielded 34 g of solid material. This was recrystallized from hexane to afford 3 (7.5 g, 46%), m.p. 92°-94° C. A second crop from recrystallization afforded additional amounts of 3 (6.9 g) contaminated with a-phenylacetophenone. The thiadiazole could be sublimed at 110° C. (0.2 mm).

Analysis: Calc'd for $C_{14}H_{10}N_2S$: C, 70.56; H, 4.23; N, 11.76; S, 13,46. Found: C, 70.68; H, 4.29; N, 12.13; S, 13.50.

EXAMPLE 10

4-(4-Methoxyphenyl)-1,2,3-thiadiazole (4)

The hydrazone (16.0 g, 68 mmol) derived from p-methoxyacetophenone and ethylcarbazate was added to 50 ml of $SOCl_2$ and cooled in an ice bath. The reaction was warmed to room temperature and then heated at 60° C. for 1 hour. The reaction was cooled, and the solvent was removed under vacuum, affording a crude solid. The solid was recrystallized from ether affording 4 (9.95 g, 76%), m.p. 91°-93.5° C.

Analysis: Calc'd for $C_9H_8N_2OS$: C, 56.22; H, 4.19; N, 14.58; S, 16.68. Found: C, 56.02; H, 4.26; N, 14.83; S, 16.83.

EXAMPLE 11

5-(1,3-Benzodioxol-5-yl)-4-phenyl-1,2,3-thiadiazole (5)

A. 2-(1,3-benzodioxyl-5-yl)-1-phenyl-ethanon (6)

To an etherial solution of phenylmagnesium bromide (100 ml, 0.3 mol, 3M in $Et_2O$) was added 1,3-benzodioxy-5-yl-acetonitrile (40.0 g, 0.248 mol) and dissolved in $Et_2O$ (500 ml). The reaction was heated at reflux for 4 hours and then let stand at room temperature for 15 hours. The reaction was quenched by adding 10 10% aqueous HCl (200 ml), then 100 ml of concentrated HCl and finally by refluxing the mixture for 1 hour. The product was extracted with $2 \times 100$ ml portions of $CH_2Cl_2$ and chromatographed (1 kilo $SiO_2$, Hex-/EtOAc—7/3) yielding 23.16 g of solid. Recrystallization from $Et_2O$ afforded 6 (11.5 g, 20%), m.p. 69°-70.5° C.

B. The hydrazone (10.8 g, 33 mmol) derived from ketone 6 and ethylcarbazate was added to 50 ml of $SOCl_2$ and heated at 60° C. for 1 hour. The solvent was removed under vacuum, and the solid was chromatographed ($SiO_2,CH_2Cl_2$) to afford crude 5. This was triturated with ether affording 2.75 g of 5, m.p.

107°–109° C. A second crop of 1.08 g was obtained, and a less pure third crop of 2.2 g was obtained.

EXAMPLE 12

4,5-Bis(p-Methoxyphenyl)-1,2,3-thiadiazole (7)

The hydrazone (7.0 g, 20 mmol) derived from desoxyanisoin (Aldrich) and ethylcarbazate was added to 20 ml of $SOCl_2$; which had been cooled in an ice bath. The reaction was heated at 60° C. for 1 hour, cooled and then the solvent was removed under vacuum. The crude residue was triturated with ether affording 7.5 g of crude material, m.p. 80°–82° C. This was recrystallized from ether affording 3.59 g (60%) of 7, m.p. 84°–86° C. as red crystals. A simple column filtration through silica afforded white, analytically pure crystals of 7, m.p. 84°–86° C.

Analysis: Calc'd for $C_{16}H_{14}N_2O_2S$: C, 64.41; H, 4.73; N, 9.93, S, 10.75. Found: C, 64.04; H, 4.72; N, 9.52; S, 10.91.

EXAMPLE 13

5-(4-Methoxyphenyl)-4-phenyl-1,2,3-thiadiazole (8)

A. Ethyl [2-(4-methoxyphenyl)-1-phenylethylidene]-hydrazine carboxylate (9)

A solution of 1-phenyl-2-(4-methoxyphenyl)-ethanone (Aldrich) (22.6 g, 0.1 mol), ethyl carbazate (12.5 g, 0.12 mol) and a spatula tip of TsOH in toluene (200 ml) was heated to reflux, and water was azeotropically removed. The reaction was complete (by TLC) after 4 hours. The solvent was removed under reduced pressure, and the crude solid was chromatographed, $SiO_2$ (400 g), eluting with Hex/EtOAc, 7/3, affording 9 (24.0 g, 76.9%).

B. 5-(4-Methoxyphenyl)-4-phenyl-1,2,3-thiadiazole (8)

The acylhydrazone 9 (4.6 g, 14.8 mol), was added to $SOCl_2$ (25 ml) at 0° C. The reaction was stirred to 60° C. and was complete (by TLC) after 1.5 hour. $SOCl_2$ was evaporated under reduced pressure and the crude oil was chromatographed on $SiO_2$ (150 g), eluting with $CH_2Cl_2$ to afford 8 (3.25 g, 82.3%), m.p. 56.5°–58° C.

Analysis: Calc'd for $C_{15}H_{12}N_2OS$: C, 67.14; H, 4.51; N, 10.44; S, 11.95. Found: C, 67.02; H, 4.50; N, 10.31; S, 12.23.

EXAMPLE 14

4-(4-methoxyphenyl)-5-phenyl-1,2,3-thiadiazole (10)

A. 1-(4-Methoxyphenyl)-2-phenylethanone (11)

Phenylacetyl chloride (30.9 g, 0.2 mol) in $CH_2Cl_2$ (100 ml) was added dropwise to a solution of $AlCl_3$ (32 g, 0.24 mol) and anisole (21.6 g, 0.2 mol) in $CH_2Cl_2$ (400 ml) at room temperature. The reaction was complete (by TLC) after 4 hours and was poured over an ice; 10% HCl slurry. The organic layer was washed with $H_2O$ and brine, dried over $MgSO_4$, and the solvent was removed under reduced pressure. The crude solid was chromatographed $SiO_2$ (1500 g), eluting with toluene to afford 11 (20.2 g, 63.7%, para isomer), m.p. 74°–75.5° C.

B. Ethyl[1-(4-methoxyphenyl)-2-phenylethylidene]-hydrazine carboxylate (12)

A solution of ketone 11 (7.6 g, 34.5 mmol), ethyl carbazate (4.38 g, 42.1 mmol) and a spatula tip of TsOH in toluene (100 ml) was heated to reflux and water azeotropically removed. The reaction was complete (by TLC) after 4 hours. The Solvent was removed under reduced pressure and the crude solid was recrystallized from EtOAc to give 12 (5.80 g, 54.2%), m.p. 121°–122.5° C.

C. 4-(4-Methoxyphenyl)-5-phenyl-1,2,3-thiadiazole (10)

The acylhydrazine 12 (23.4 g, 75.0 mmol) was added to $SOCl_2$ (200 ml) at 0° C. The reaction was warmed to 60° C. and complete (by TLC) after 3 hours. $SOCl_2$ was removed under reduced pressure. The solid residue was dissolved in EtOAc, washed once with 10% aqueous NaOH and brine. The organic layer was dried over $MgSO_4$, and the solvent was removed under reduced pressure. The crude solid was recrystallized from $Et_2O$ to afford 10 (13.0 g, 64.6%), m.p. 81.5°–82.5° C.

Analysis: Calc'd for $C_{15}H_{12}N_2OS$: C, 67.14; H, 4.51; N, 10.44; S, 11.95. Found: C, 66.96; H, 4.59; N, 10.75; S, 12.07.

EXAMPLE 15

4-(2,4-dimethoxyphenyl-5-(4-methoxyphenyl-1,2,3-thiadiazole (13)

A. 1-(2,4-Dimethoxyphenyl)-2-(4-methoxyphenyl)-ethanone (14)

P-Methoxyphenylacetyl chloride (33.2 g, 0.18 mol) in $CH_2Cl_2$ (100 ml) was added dropwise to a solution of $AlCl_3$ (28.8 g, 0.21 mol) and m-dimethoxybenzene (24.9 g, 0.18 mol) in $CH_2Cl_2$ (400 ml). The reaction wad complete (by TLC) after 1 hour and was poured over 10% HCl:ice slurry. The organic layer was washed with $H_2O$ and brine, dried over $MgSO_4$, and the solvent was removed under reduced pressure. The crude solid was recrystallized from ether/methanol to afford 14 (38.5 g, 74.8%), m.p. 78.5°–79.5° C.

B. Ethyl-[1-(2,4-dimethoxyphenyl)-2-(4-methoxyphenyl)-ethylidene]hydrazine carboxylate (15)

A solution of ketone 14 (22.7 g, 79.5 mmol) ethyl carbazate (9.92 g, 95.4 mmol) and a spatula tip of TsOH in toluene (200 ml) was heated to reflux, and the water was azeotropically removed. The reaction was complete (by TLC) after 4 hours. The solvent was removed under reduced pressure and the crude oil was triturated with hexane, affording a solid which was then recrystallized from $Et_2O$/EtOAc to yield 15 (14.1 g, 47.8%), m.p. 104°–105.5° C.

C. 4-(2,4-Dimethoxyphenyl)-5-(4-methoxyphenyl)-1,2,3-thiadiazole (13)

Acylhydrazone 15 (4.32 g, 11.6 mmol) was added to $SOCl_2$ (50 ml) at 0° C. The reaction was allowed to warm to room temperature. The reaction was complete (by TLC) after 3 hours. $SOCl_2$ was removed under reduced pressure and the crude brown oil was chromatographed on 350 g $SiO_2$, eluting with 4:1, $CH_2Cl_2$:Hexane to afford 13 (1.7 g, 44.7%), m.p. 90-91.5.

Analysis: Calc'd for $C_{17}H_{16}N_2O_3S$: C, 61.96; H, 4.89; N, 8.50; S, 9.73. Found: C, 62.14; H, 4.93; N, 8.38; S, 9.60.

EXAMPLE 16

5-(4-anisyl)-4-(thiophen-2-yl)-1,2,3-thiadiazole (16)

A. 2-(4-Methoxyphenyl)-1-(2-thienyl)-ethanone (17)

p-Methoxyphenylacetyl chloride (36.9 g, 0.2 mol) and thiopene (16.8 g, 0.2 mol) in $CH_2Cl_2$ (400 ml) was cooled to 0° C. Stannic chloride (52.1 g, 0.2 mol) in $CH_2Cl_2$ (100 ml) was added dropwise. The resulting green solution was quenched after 3 hours by pouring the mixture over a 10% HCl/ice slurry. The organic layer was washed with water and brine, dried over MgSO$_4$, and the solvent was removed under reduced pressure. The solid residue was recrystallized from ether to afford 17 (32.0 g, 68.9%), m.p. 77°–78.4° C.

B. Ethyl-[2-(4-methoxyphenyl)-1-(2-thiophenyl)ethylidene]hydrazine carboxylate (18)

A solution of ketone 17 (6.0 g, 25.9 mmol), ethyl carbazate (3.2 g, 31.0 mmol) and a spatula tip of TsOH in toluene (100 ml) was heated to reflux and water was azeotropically removed. The reaction was complete (by TLC) after 3.5 hours. The Solvent was removed under reduced pressure, and the crude oil was chromatographed on SiO$_2$ (300 g), eluting with CH$_2$Cl$_2$ to afford 18 (2.9 g, 35.2%)

C. 5-(4-Anisyl)-4-(thiophen-2-yl)-1,2,3-thiadiazole (16)

Acylhydrazine 18 (45 g, 0.14 mol) was added to SOCl$_2$ (200 ml) at 0° C. The solution was allowed to warm to room temperature. The reaction was complete (by TLC) after 2.5 hours. SOCl$_2$ was removed under reduced pressure. The dark brown oil was dissolved in EtOAc and washed twice with H$_2$O, dried over MgSO$_4$, and the solvent was removed under reduced pressure. The resulting oil was chromatographed on SiO$_2$ (1 kg) eluting with Hexane/CH$_2$Cl$_2$, 1/1, and then recrystallized from ether to afford 16 (12.8 g, 33.4%), m.p. 81.0–82.0

Analysis: Calc'd for C$_{13}$H$_{10}$N$_2$OS$_2$: C, 56.91; H, 3.67; N, 10.21; S, 23.37. Found: C, 56.66; H, 3.70; N, 10.61; S, 23.22.

EXAMPLE 17

5-Anisyl-4-(fur-2-yl)-1,2,3-thiadiazole (19)

A. 1-(2-Furyl)-2-(4-methoxyphenyl)-ethanone (20)

Furan (5 g, 73.5 mmol) in CH$_2$Cl$_2$ (10 ml) was added to a solution of p-methoxyphenylacetyl chloride (2.21 g, 14.7 mmol) and trifluoromethanesulfonic acid (150 μl) in CH$_2$Cl$_2$ (25 ml) at reflux. The reaction was quenched after 3 hours by pouring the solution over a 10% HCl/ice slurry. The organic layer was washed with 10% aqueous NaOH, dried over MgSO$_4$, and the solvent was removed under reduced pressure. The crude oil was chromatographed ion SiO$_2$ (85 g). eluting with Hexane/EtOAc, 4/1, to give 20 (1.12 g, 35.3%) 41.5°–43.0° C.

B. Ethyl-[1-(2-furyl)-2-(4-methoxyphenyl)ethylidene]hydrazine carboxylate (21)

A solution of ketone 20 (5.7 g, 26.4 mmol), ethyl carbazate (2.83 g, 27.1 mol) and a spatula tip of TsOH in toluene (120 ml) was heated to reflux, and the water was azeotropically removed. The reaction was complete (by TLC) after 4 hours. The solvent was removed under reduced pressure, and the crude residue was chromatographed on SiO$_2$ (150 g), eluting with Hexane/EtOAc, 2/1 to afford 21 (3.36 g, 43.9%).

C. 5-Anisyl-4-(fur-2-yl)-1,2,3-thiadiazole

Acylhydrazone 21 (3.36 g, 11.6 mmol) was cooled to 0° C. and SOCl$_2$ (25 ml) was added. The reaction was kept at 0° C. and was complete (by TLC) after 0.75 hour. The reaction was poured over 300 g ice and the aqueous solution extracted twice with EtOAc. The organic fractions were dried over MgSO$_4$, and the solvent was removed under reduced pressure. The residual oil was chromatographed on SiO$_2$ (200 g) eluting with Hexane/EtOAc, 3/1, to afford 19 (0.94 g, 85.0%, based on unrecovered staring material), m.p. 80.6°–82.0° C.

Analysis: Calc'd for C$_{13}$H$_{10}$N$_2$O$_2$S: C, 60.45; H, 3.90; N, 10.85; S, 12.41. Found: C, 60.16; H, 3.91; N, 10.30; S, 11.92.

EXAMPLE 18

4-(4-Anisyl-5-(thiophen-2-yl)-1,2,3-thiadiazole (22)

A. 1-(4-Methoxyphenyl)-2-(2-thiophenyl)-ethanone (23)

2-Thiophenylacetyl chloride (12.38 g, 77.1 mmol) in CH$_2$Cl$_2$ (40 ml) was added to a solution of anisole (8.33 g, 77.1 mmol) and AlCl$_3$ (10.3 g, 77.1 mmol) in CH$_2$Cl$_2$ (200 ml) at room temperature. The reaction was completed after 2 hours, and the mixture was poured over a 10% HCl/ice slurry. The organic layer was washed with H$_2$O and brine, dried over MgSO$_4$, and the solvent was removed under reduced pressure. The crude solid was chromatographed on SiO$_2$ (1 kg) eluting with CH$_2$Cl$_2$/Hexane, 3/1, to afford 23 (9.37 g, 52.4%), m.p. 44.0°–45.5° C. and the ortho isomer (2.14 g, 12%)

B. Ethyl[1-(4-methoxyphenyl)-2-(2-(thiophenyl)-ethylidene]hydrazine carboxylate (24)

A solution of ketone 23 (7.37 g, 31.7 mmol), ethyl carbazate (3.31 g, 31.7 mmol) and a spatula tip of TsOH in toluene (100 ml) was heated to reflux, and the water was azeotropically removed. The reaction was complete (by TLC) after 2 hours. The solvent was removed to give a yellow oil 24 (9.7 g, 96.2%), which was homogenous by TLC and greater than 90% pure by NMR.

C. 4-(4-Anisyl)-5-(thiophen-2-yl)-1,2,3-thiadiazole (22)

Acylhydrazone 24 (10.5 g, 33.0 mmol) was cooled to 0° C. and SOCl$_2$ (100 ml) was added. The reaction was allowed to warm to room temperature and was complete (by TLC) after 1 hour. SOCl$_2$ was removed under reduced pressure, and the residue oil was chromatographed on SiO$_2$ (400 g) eluting with CH$_2$Cl$_2$/Hexane, 2/1. The isolated yellow solid was recrystallized from ether to afford 22 (3.5 g, 38.5%), m.p. 72.2°–73.3° C.

Analysis: Calc'd for C$_{13}$H$_{10}$N$_2$OS$_2$: C, 56.91; H, 3.67; N, 10.21; S, 23.37. Found: C, 56.74; H, 3.68; N, 10.54; S, 23.49.

EXAMPLE 19

5-(4-methoxyphenyl-4-(4-thiomethylphenyl)-1,2,3-thiadiazole (25)

A. 2-(4-Methoxyphenyl)-1-(4-thiomethylphenyl)-ethanone (26)

p-Methoxyphenylacetyl chloride (5.0 g, 27.1 mmol) in CH$_2$Cl$_2$ (20 ml) was added to a solution of thioanisole (3.36 g, 27.1 mmol) and AlCl$_3$ (3.61 g, 27.1 mmol) in CH$_2$Cl$_2$ (100 ml). The reaction was complete (by TLC) after 3 hours, and the mixture was poured over a 10% HCl/ice slurry. The organic layer was removed, washed with H$_2$O and brine, dried over MgSO$_4$, and the solvent was removed under reduced pressure. The crude solid was chromatographed on SiO$_2$ (150 g), eluting with CH$_2$Cl$_2$/Hexane, 1/1, to afford 26 (2.8 g, 38%), m.p. 127.2°–129.5° C. and the ortho isomer (2.1 g, 29%).

B. Ethyl-[2-(4-methoxyphenyl)-1-(4-thiomethylphenyl)-ethylidene]hydrazine carboxylate (27)

A solution of ketone 26 (5.74 g, 21.1 mmol) ethyl carbazate (2.31 g, 22.1 mmol) and a spatula tip of TsOH in toluene (100 ml) was heated to reflux, and the water was azeotropically removed. The reaction was complete (by TLC) after 3hours, and the solvent was removed under reduced pressure to afford 27 (7.40 g. 97%) m.p. 120.0°-122.5° C.

C. 5-(4-Methoxyphenyl)-4-(4-thiomethylphenyl)-1,2,3-thiadiazole (25)

The acylhydrazone 27 (7.6 g, 21.3 mmol) was added to $SOCl_2$ (80 ml) at 0° C. The reaction was warmed to room temperature and stirred overnight. The solvent was removed under reduced pressure. The brown oil was taken up in $CH_2Cl_2$ and washed twice with $H_2O$, dried over $MgSO_4$, and the solvent was removed under reduced pressure. The brown solid was recrystallized from ether/EtOAc to afford 25 (3.8 g, 63.3%), m.p. 117.2°-118.9° C.

Analysis: Calc'd for $C_{16}H_{14}N_2OS_2$: C, 61.21; H, 4.49; N, 8.91; S, 20.39. Found: C, 60.87; H, 4.52; N, 9.10; S, 20.32.

EXAMPLE 20

4,5-Bis-(4-hydroxyphenyl)-1,2,3-thiadiazole (28)

Boron tribromide (102 ml of a 1 M solution in $CH_2Cl_2$) was added dropwise to a solution of thiadiazole 7 (8.0 g, 26.84 mmol) in $CH_2Cl_2$ (30 ml) at −78° C. After 2 hours the resulting dark green solution was warmed to 0° C. and quenched with 5% HCl. The aqueous layer was extracted twice with EtOAc. The organic layers were combined, dried over $MgSO_4$, and the solvent was removed under reduced pressure. The crude yellow solid was dissolved in EtOAc and extracted twice with 5% NaOH. The aqueous layer was acidified with 10% HCl, and extracted twice with EtOAc. The organic layers were combined, dried over $MgSO_4$, and the solvent was removed under reduced pressure. The resulting white solid was recrystallized from $MeOH/H_2O$ to afford 28 (5.58 g, 77.1%), m.p. 221.0°-222.0°60 C.

Analysis: Calc'd for $C_{14}H_{10}N_2O_2S$: C, 62.21; H, 3.73; N, 10.36; S, 11.86. Found: C, 62.06; H, 3.86; N, 10.60; S, 11.97.

EXAMPLE 21

4,5-Bis(2-thienyl)-1,2,3-thiadiazole (29)

A. 1,2-Bis-(2-thienyl)-ethanone (30)

$SnCl_4$ (1.01 g, 3.94 mmol) in $CH_2Cl_2$ (5 ml) was added to 2-thiophenylacetyl chloride (6.33 g, 39.4 mmol) and thiopene (3.32 g, 39.4 mmol) in $CH_2Cl_2$ (300 ml) at room temperature. The reaction was complete (by TLC) after 3 hours. The solution was poured over a 10% aqueous HCl/ice slurry. The organic layer was separated, washed twice with $H_2O$ and dried over $MgSO_4$. The solvent was removed under reduced pressure. The crude oil was chromatographed on $SiO_2$ (300 g), eluting with Hexane/$CH_2Cl_2$, 1/1 to afford 30 (3.3 g, 40.5%).

Ethyl[1,2-bis-(2-thienyl)-ethylidene]hydrazine carboxylate (31)

A solution of ketone 30 (4.0 g, 19.1 mmol) ethyl carbazate (2.11 g, 20.0 mmol) and a spatula tip of TsOH in toluene (120 ml) was heated to reflux, and the water was azeotropically removed. The reaction was complete (by TLC) after 2 hours. The solvent was removed under reduced pressure. The crude solid was washed with ether and dried to afford 31 (4.12 g, 73.3%).

C. 4,5-Bis-(2-thienyl)-1,2,3-thiadiazole

Acylhydrazine 31 (14.13 g, 14.04 mmol) was added to $SOCl_2$ (60 ml) at 0° C. The reaction was allowed to warm to room temperature. The reaction was complete (by TLC) after 2 hours. $SOCl_2$ was removed under reduced pressure. The dark residue was chromatographed on $SiO_2$ (300 g), eluting with $CH_2Cl_2$. The isolated oil was bulb to bulb distilled at 0.2 mm (Hg) at 150° C. to yield 29 (2.3 g, 66.0%).

Analysis: Calc'd for $C_{10}H_6N_2S$: C, 47.48; H, 2.41; N, 11.19; S, 38.42. Found: C, 47.53; H, 2.43; N, 11.31; S, 38.77.

EXAMPLE 22

4,5-Bis-(4-aminophenyl)-1,2,3-thiadiazole (32)

A. Anilino-(4-nitrophenyl)-diphenylphosphonomethane (33)

A solution p-nitrobenzaldehyde (50.0 g, 0.33 mol), aniline (30.0 g, 0.33 mol) and a spatula tip of TsOH in toluene (500 ml) was heated to reflux, and the water was azeotropically removed. After 2 hours the solution was cooled to 0° C. and diphenyl phosphite in toluene (100 ml) was added. The solution was warmed to room temperature and stirred for 1 hour. The flask contents were filtered and washed with ether to afford 33 (112.2 g, 73.9%), m.p. 158°-159.9° C.

B. 1,2-Bis-(4-nitrophenyl)-ethanone (34)

A solution of KOH (7.56 g, 0.13 mol) in MeOH (75 ml) was added to the phosphonate ester 33 (62.1 g, 0.13 mol) in THF (400 ml) at −78° C. for 0.5 hour and p-nitrobenzaldehyde (20.3 g, 0.13 mol) in 200 ml of THF was added over 0.5 hour. The reaction was warmed to room temperature and stirred an additional 2 hours. THF was removed under reduced pressure. The residue was taken up in EtOAc and washed twice with 5% aqueous $NaHCO_3$ and once with brine. The ethyl acetate was removed under reduced pressure. The dark red enemine was dissolved in $CH_3OH$ (600 ml) and concentrated HCl (0.2 ml) was added. The solution was stirred for 1 hour at room temperature and diluted with $H_2O$ (500 ml). The solid was filtered, washed with ether and dried to afford 34 (35.6 g, 82.0%), m.p. 131°-133° C.

C. Ethyl[1,2-bis-(4-nitrophenyl)-ethylidene]hydrazine carboxylate (35)

A solution of ketone 34 (30 g, 10.5 mmol), ethyl carbazate (11.6 g, 10.7 mmol), and a spatula tip of TsOH in toluene (300 ml) was heated to reflux, and the water was azeotropically removed. The reaction was complete (by TLC) in 3 hours. The solution was cooled to 0° C. and filtered. The mother liquor was concentrated and the oil triturated with hexane, forming a solid which was recrystallized from ether to afford 35 (29.1 g, 77.6%), m.p. 184°-187° C.

D. 4,5-Bis-(4-nitrophenyl)-1,2,3-thiadiazole (36)

Acylhydrazone 35 (21 g, 58.7 mmol) was added to $SOCl_2$ (80 ml) at 0° C. The temperature was increased to 50° C., and the reaction was complete (by TLC) after 4 hours. $SOCl_2$ was removed under reduced pressure. The crude solid was recrystallized from ETOAc/MeOH to afford 36 (11.6 g, 60.3%) m.p. 185°-186.5° C.

E. 4,5-Bis-(4-aminophenyl)-1,2,3-thiadiazole (32)

Thiadiazole 36 (11.8 g, 36.1 mmol) in EtOH (200 ml) was hydrogenated over 5% Pd/C (3.6 g) at 50 psi for 16 hours. The solution was filtered through a celite pad and washed with EtOH. The solvent was removed under reduced pressure, and the crude solid was recrystallized from EtOAc/MeOH to afford 32 (9.2 g, 95.1%), m.p. 236° C. (decomposes).

EXAMPLE 23

4,4'-(1,2,3-Thiadiazole-4,5-diyl)-bis-dihydrochloride benzenamine (32.2HCl)

Thiadiazole 32 (2.0 g, 7.46 mmol) was dissolved in MeOH (150 ml). The solution was saturated with HCl gas at room temperature and stirred an additional 0.5 hour. The solution was diluted 4 fold with ether and filtered to afford 32.2HCl (2.23 g, 87.8%) m.p. 243° C. (decomposes).

Analysis: Calc'd for $C_{14}H_{14}Cl_2N_4S$: C, 49.27; H, 41.3; N, 16.42; S, 9.39. Found: C, 48.94; H, 3.73; N, 16.40; S, 93.6.

EXAMPLE 24

4,5-Bis-[4-(N-ethylamino)-phenyl]-1,2,3-thiadiazole (37)

$NaBH_4$ pellets (2.55 g, 67.1 mmol) were slowly added to thiadiazole 32 (1.8 g, 6.71 mmol) in HOAc (25 ml). The reaction temperature was kept constant at 15° C. during the addition. The reaction was stirred for 0.5 hour and cooled to 0° C. The solution was brought to pH 10 by addition of NaOH pellets. The aqueous solution was extracted 3 times with EtOAc. The organic layers were combined, dried over $MgSO_4$, and the solvent was removed under reduced pressure. The crude solid was chromatographed on $SiO_2$ (100 g), eluting with Hexane/EtOAc, 4/1. The isolated solid was recrystallized from ether/EtOAc to afford 37 (0.95 g, 44.0%), m.p. 96.5°–98.5° C.

Analysis: Calc'd for $C_{18}H_{20}N_4S$: C, 66.64; H, 6.21; N, 17.27; S, 9.88. Found: C, 66.94; H, 6.19; N, 16.75; S, 9.62.

EXAMPLE 25

4,5-Bis-[4-(N,N-dimethyl)-phenyl]-1,2,3-thiadiazole (38)

A slurry of thiadiazole 32 (1.26 g, 4.7 mmol) and $NaBH_4$ (2.06 g, 54 mmol) in THF (40 ml) was added to a solution of THF (60 ml), 3M $H_2SO_4$ (5 ml) and formalin (3.34 ml, 39 mmol) at 15° C. The reaction was kept at pH 4 by addition of 3M $H_2SO_4$. The reaction was stirred for 1 hour and quenched with 25% aqueous NaOH at 0° C. The aqueous layer was extracted twice with EtOAc. The organic layers were combined, dried over $MgSO_4$, and the solvent was removed under reduced pressure. The solid was recrystallized from ether to afford 38 (1.06 g, 72.1%), m.p. 152.5°–154°60 C.

Analysis: Calc'd for $C_{18}H_{20}N_4S$: C, 66.64; H, 6.21; N, 17.27; S, 9.88. Found: C, 66.89; H, 6.15; N, 16.98; S, 9.78.

In Scheme II the reaction of (A) to (B) and (B) to (C) are well known in the art.

The reaction of (C) to (E) is disclosed by Hurd and Mori, J. Am. Chem. Soc. 77, pp. 5359–5304 (1955). Other anhydrous solvents can be benzene, toluene and the like at reflux temperatures with azeotropic removal of water.

The reaction of (C) to (D) as exemplified is carried out with the mixture of ketone, ethyl carbazate and catalytic amount of toluene sulfonic acid in toluene at reflux temperature, with azeotropic removal of water. The solvents are removed under reduced pressure, and the crude solids recrystallized form ethyl acetate-ether, hexane, or ethyl acetate as exemplified.

Other suitable solvents can be, for the reaction, benzene, ethanol, or methanol. For recrystallization, ethyl acetate, diethyl ether, or ethyl acetate:hexane can be used.

The reaction of (D) or (E) to give the final product (F) is carried out in thionyl chloride, which serves as both reagent and solvent. If co-solvents, e.g., methylene chloride are used, lower yields occur.

The reaction can be at 60° C. for 1 hour or ambient temperature for up to 24 hours. The reaction is further illustrated by Radp and Micetich, Can. J. Chem. 40, pp. 1057–1063 (1968) at p. 1062, third paragraph.

The conditions illustrated in Scheme III are preferred over the literature methods due to increase yield of product (C).

SCHEME I

Compounds of the Formula I are novel compounds of the present invention. Compounds of the Formula II represent known compounds.

FORMULA I

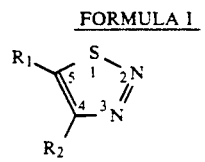

Formula I $R_1$ and $R_2$ are the same of different and are selected from the group consisting of

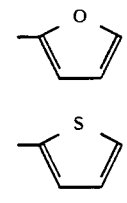

or

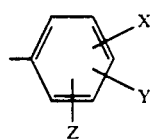

wherein X, Y and Z are hydrogen, —$OR_3$, —$SR_4$ or

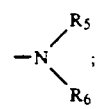

and X and Y taken together can be

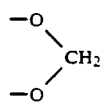

wherein the oxygen atoms are bonded to adjacent ring atoms
wherein $R_3$, $R_4$, $R_5$ and $R_6$ are the same or different and are hydrogen or alkyl of from 1 to 5 carbon atoms, inclusive; provided that when $R_1$ and $R_2$ are either R₁ or R₂ is at least monosubstituted;

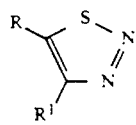

Formula II

R and R' are different, and one is hydrogen, and one is selected from the group consisting of

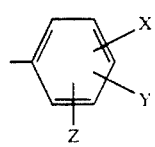

wherein X, Y and Z are the same or different and are hydrogen or OR", and R" is hydrogen or alkyl of from 1 to 5 carbon atoms, inclusive.

SCHEME II

The following flow diagram illustrates the chemical synthesis of the compounds of the present invention starting with the known compounds A and B.

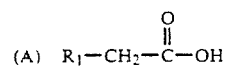

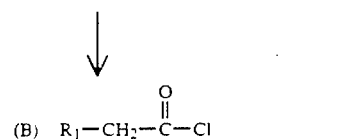

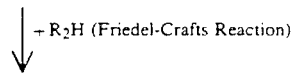

↓ + R₂H (Friedel-Crafts Reaction)

↓

-continued

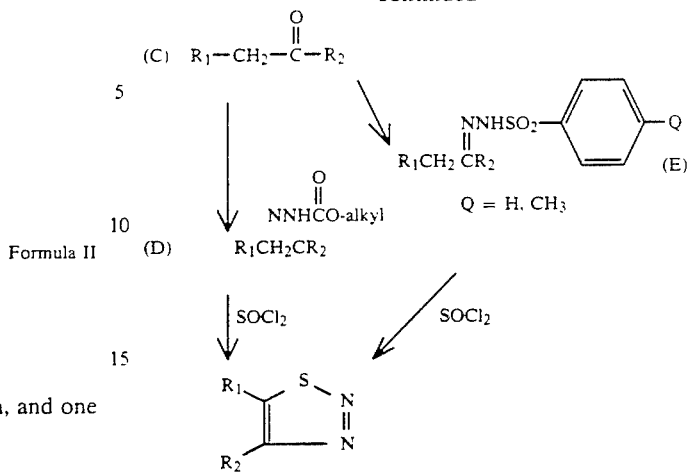

$Q = H, CH_3$

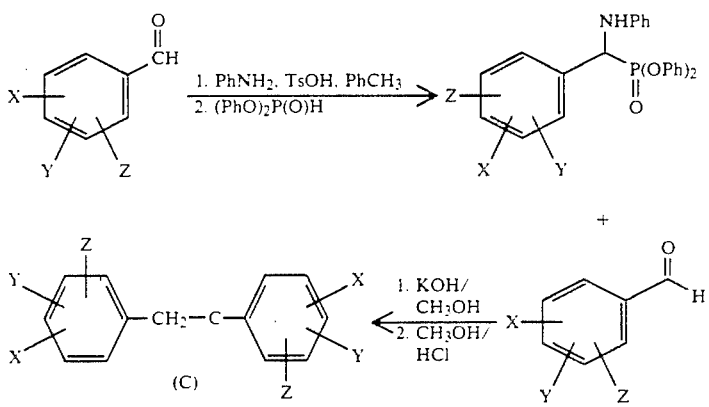

$R_1$ and $R_2$ are defined as per Formula I.

When $R_1$ and/or $R_2$ contain an amino substituent, said substituent is derived from the corresponding nitro group. For that special case the corresponding intermediate C is prepared as illustrated in Scheme III.

SCHEME III

X, Y and Z are the same or different, chosen from the groups H and $NO_2$.

Intermediate (C) is then reacted according to Scheme II to give the corresponding nitrated phenyl-1,2,3-thiadiazole. The nitro groups are reduced catalytically ($H_2$, EtOH, 5% Pd/C), and the resulting primary amine groups are alkylated, if desired, according to standard procedures.

What is claimed:

1. A compound of the formula

Formula I $R_1$ and $R_2$ are the same or different and are selected from the group consisting of

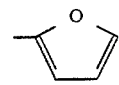

-continued

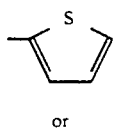

or

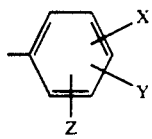

wherein X, Y and Z are hydrogen, —OR$_3$, —SR$_4$ or

and X and Y taken together can be

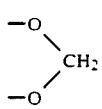

wherein the oxygen atoms are bonded to adjacent ring atoms
wherein R$_3$, R$_4$, R$_5$ and R$_6$ are the same or different and are hydrogen or alkyl of from 1 to 5 carbon atoms, inclusive; provided that when R$_1$ and R$_2$ are

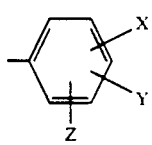

either R$_1$ or R$_2$ is at least monosubstituted, with the further proviso that when R$_2$ is alkoxyphenyl, R$_1$ is not phenyl, when R$_2$ is phenyl, R$_1$ is not monohydroxyphenyl, and when R$_2$ is 4-methoxyphenyl, R$_1$ is not 2-methoxyphenyl.

2. A compound of claim 1 wherein R$_1$ and R$_2$ are the same or different and are selected form the group consisting of

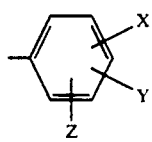

wherein X, Y and Z are hydrogen, —OR$_3$ or —SR$_4$; wherein R$_3$ and R$_4$ are the same or different and are hydrogen or alkyl of from 1to 5 carbon atoms, inclusive; provided wither R$_1$ or R$_2$ is at least monosubstituted, with the further proviso that when R$_2$ is alkoxyphenyl, R$_1$ is not phenyl, when R$_2$ is phenyl, R$_1$ is not monohydroxyphenyl, and when R$_2$ is 4-methoxyphenyl, R$_1$ is not 2-methoxyphenyl.

3. A compound of claim 2 which is 4,5-bis-(4-methoxyphenyl)-1,2,3-thiadiazole.

4. A compound of claim 1 wherein R$_3$, R$_4$, R$_5$ and R$_6$ are the same or different and are hydrogen or alkyl of from 1 to 5 carbon atoms, inclusive; provided that when R$_1$ and R$_2$ are

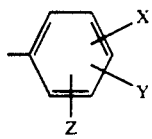

either R$_1$ or R$_2$ is at least monosubstituted and further provided that X, Y and Z are not hydrogen, —OR$_3$ or —SR$_4$, unless either R$_1$ or R$_2$ is at least monosubstituted with

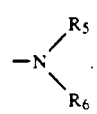

5. A compound of claim 4 which is 4,4'-(1,2,3-thiadiazole-4,5-diyl)bis(N,N-dimethyl)-benzenamine.

6. A pharmaceutical composition in unit dosage form comprising an effective platelet aggregation inhibiting amount of a compound selected from the group consisting of compounds of formula

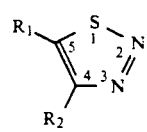

Formula I

R$_1$ and R$_2$ are the same or different and are selected from the group consisting of

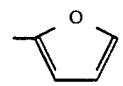

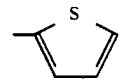

or

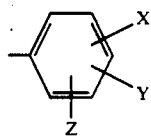

wherein X, Y and Z are hydrogen, —OR$_3$, —SR$_4$ or

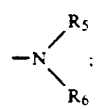

and X and Y taken together can be

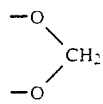

wherein the oxygen atoms are bonded to adjacent ring atoms
wherein $R_3$, $R_4$, $R_5$ and $R_6$ are the same or different and are hydrogen or alkyl of from 1 to 5 carbon atoms, inclusive; provided that when $R_1$ and $R_2$ are

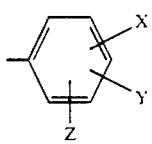

either $R_1$ or $R_2$ is ate least monosubstituted, with the further proviso that when $R_2$ is alkoxyphenyl, $R_1$ is not phenyl;
or a compound of the formula

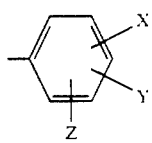

Formula II wherein R and R' are either both phenyl or one is hydrogen, and one is selected from the group consisting of

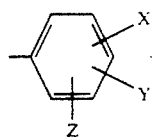

wherein X, Y and Z are the same or different and are hydrogen or OR'', and R'' is hydrogen or alkyl of from 1 to 5 carbon atoms, inclusive, in association with a pharmaceutical carrier.

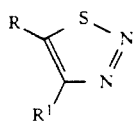

7. A pharmaceutical composition according to claim 6 wherein $R_1$ and $R_2$ are the same or different and selected from the group consisting of
   wherein X, Y and Z are hydrogen, —OR_3 or —SR_4;
   wherein $R_3$ and $R_4$ are the same or different and are hydrogen or alkyl of from 1 to 5 carbon atoms, inclusive; provided either $R_1$ or $R_2$ is at least monosubstituted, in association with a pharmaceutical carrier.

8. A composition according to claim 6 wherein the compound selected is 4,4'-bis-(1,2,3-thiadiazole-4,5-diyl)bis(N,N-dimethyl)-benzeneamine or 4,5-bis-(4-methoxyphenyl)-1,2,3-thiadiazole.

9. A process of inhibiting platelet aggregation in vitro comprising the addition of an effective platelet aggregation inhibiting amount a compound of the formula

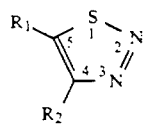

Formula I $R_1$ and $R_2$ are the same or different and are selected from the group consisting of

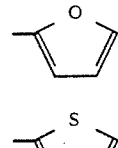

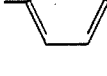

or

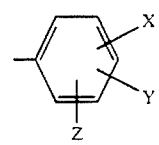

wherein X, Y and Z are hydrogen, —OR_3, —SR_4 or

and X and Y taken together can be

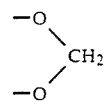

wherein the oxygen atoms are bonded to adjacent ring atoms
wherein $R_3$, $R_4$, $R_5$ and $R_6$ are the same or different and are hydrogen or alkyl of from 1 to 5 carbon atoms, inclusive; provided that when $R_1$ and $R_2$ are

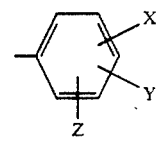

either $R_1$ or $R_2$ is at least monosubstituted;
or a compound of the formula

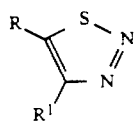

Formula II

R and R' are either both phenyl or one is hydrogen, and one is selected from the group consisting of

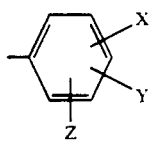

wherein X, Y and Z are the same or different and are hydrogen or OR", and R" is hydrogen or alkyl of from 1 to 5 carbon atoms, inclusive, to whole blood or platelet rich plasma concentrates.

10. The process of claim 9 wherein the compound added is 4,5-bis-(4-methoxyphenyl)-1,2,3-thiadiazole or 4,4'-(1,2,3-thiadiazole-4,5-diyl)bis(N,N-dimethyl)-benzeneamine.

11. A process of prophylactic or therapeutic treatment of platelet aggregation, comprising the systemic administration to a human or animal of an effective platelet aggregation inhibition amount of a compound selected from the group consisting of compounds of the formula

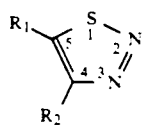

Formula I $R_1$ and $R_2$ are the same or different and are selected from the group consisting of

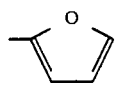

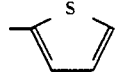

or

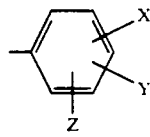

wherein X, Y and Z are hydrogen, $-OR_3$, $-SR_4$ or

and X and Y taken together can be

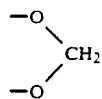

wherein the oxygen atoms are bonded to adjacent ring atoms wherein $R_3$, $R_4$, $R_5$ and $R_6$ are the same or different and are hydrogen or alkyl of from 1 to 5 carbon atoms, inclusive; provided that when $R_1$ and $R_2$ are

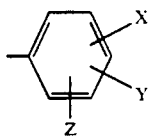

either $R_1$ or $R_2$ is at least monosubstituted, or a compound of the formula

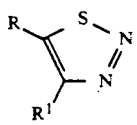

Formula II

R and R' are either both phenyl or one is hydrogen, and on is selected from the group consisting of

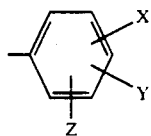

wherein S, Y and Z are the same or different and are hydrogen or OR", and R" is hydrogen or alkyl of from 1 to 5 carbon atoms, inclusive, in association with a pharmaceutical carrier.

12. A process according to claim 11 wherein the compound selected is 4,5-bis-(4-methoxyphenyl)-1,2,3-thiadiazole or 4,4'-(1,2,3-thiadiazole-4,5-diyl)bis(N,N-dimethyl)-benzenamine.

13. A process of prophylactic or therapeutic treatment of thrombotic disease states comprising the systemic administration to a human or animal of an effective platelet aggregation inhibiting amount of a compound selected from the group consisting of compounds of the formula

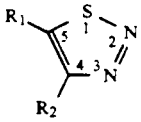

Formula I $R_1$ and $R_2$ are the same or different and are selected from the group consisting of

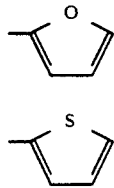

or

-continued

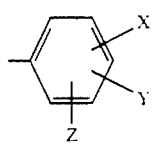

wherein X, Y and Z are hydrogen, —OR$_3$, —SR$_4$ or

and X and Y taken together can be

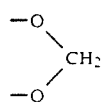

wherein the oxygen atoms are bonded to adjacent ring atoms
wherein R$_3$, R$_4$, R$_5$ and R$_6$ are the same or different and are hydrogen or alkyl of from 1 to 5 carbon atoms, inclusive; provided that when R$_1$ and R$_2$ are

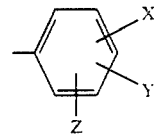

either R$_1$ or R$_2$ is at least monosubstituted, or a compound of the formula

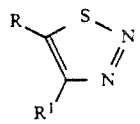

Formula II

R and R' are either both phenyl or one is hydrogen, and one is selected from the group consisting of

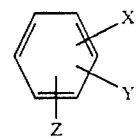

wherein X, Y and Z are the same or different and are hydrogen or OR'', and R'' is hydrogen or alkyl of from 1 to 5 carbon atoms, inclusive, in association with a pharmaceutical carrier.

14. The process of claim 11 wherein the compound is 4,5-bis-(4-methoxyphenyl)-1,2,3-thiadiazole.

* * * * *